United States Patent
Hayward et al.

(10) Patent No.: US 7,040,167 B2
(45) Date of Patent: May 9, 2006

(54) METHOD AND APPARATUS FOR DETECTING HOLES IN PLASTIC CONTAINERS

(75) Inventors: Donald W. Hayward, Waterville, OH (US); David A. Bogstad, Perrysburg, OH (US); Donald Wayne Miller, Waterville, OH (US)

(73) Assignee: Plastic Technologies, Inc., Holland, OH (US)

( * ) Notice: Subject to any disclaimer, the term of this patent is extended or adjusted under 35 U.S.C. 154(b) by 87 days.

(21) Appl. No.: 10/493,730

(22) PCT Filed: Oct. 31, 2002

(86) PCT No.: PCT/US02/34933

§ 371 (c)(1),
(2), (4) Date: Apr. 26, 2004

(87) PCT Pub. No.: WO03/038392

PCT Pub. Date: May 8, 2003

(65) Prior Publication Data

US 2005/0181087 A1    Aug. 18, 2005

Related U.S. Application Data

(63) Continuation-in-part of application No. 10/334,362, filed on Nov. 1, 2001, now Pat. No. 6,553,809.

(51) Int. Cl.
*G01N 29/00* (2006.01)
*B29C 41/52* (2006.01)

(52) U.S. Cl. ......................... 73/592; 425/169

(58) Field of Classification Search ............ 73/40, 73/40.5 R, 41, 45, 45.1–45.4; 425/169, 135, 425/136, 139

See application file for complete search history.

(56) References Cited

U.S. PATENT DOCUMENTS

| | | | | |
|---|---|---|---|---|
| 3,290,922 A | * | 12/1966 | Thompson | ..................... 73/52 |
| 3,298,518 A | * | 1/1967 | Milholland | ................. 209/559 |
| 3,399,563 A | | 9/1968 | Helms | |
| 3,795,137 A | | 3/1974 | Lo et al. | |
| 3,805,226 A | | 4/1974 | Holloway | |
| 3,841,468 A | | 10/1974 | Eggert | |
| 4,096,736 A | | 6/1978 | Moshier | |
| 4,116,043 A | * | 9/1978 | Pencak | ......................... 73/40 |
| 4,677,679 A | | 6/1987 | Killion | |
| 5,361,636 A | * | 11/1994 | Farstad et al. | ................. 73/592 |
| 6,416,308 B1 | * | 7/2002 | Pena | ......................... 425/169 |

OTHER PUBLICATIONS

Jervmo et al., International Patent Application publication WO 97/37724 "A communication interface for Breathing Equipment", Oct. 16, 1997.*
http://www.nohken.com/overseas/af.htm.*

* cited by examiner

*Primary Examiner*—Charles Garber
(74) *Attorney, Agent, or Firm*—Fraser Martin & Miller LLC; Donald R. Fraser

(57) ABSTRACT

A method and an apparatus for monitoring the production of blow molded plastic containers (20) includes a columnator (26) and sound detector (24) responsive to a defect sound of pressure fluid escaping from a container being formed in a mold cavity (14). The columnator is effective to filter the defect sound from ambient noise. An output signal generated by the sound detector is processed to generate a control signal used to reject a defective container. Preferably, the open end of the columnator is positioned between 20° and 150° from the preform loading station in a rotary platform (12) blow molding machine.

20 Claims, 2 Drawing Sheets

METHOD AND APPARATUS FOR DETECTING HOLES IN PLASTIC CONTAINERS

BACKGROUND OF THE INVENTION

1. Field of the Invention

The invention relates to a method and apparatus for monitoring the production of plastic blow molded containers. More particularly, the invention contemplates the sensing of two general classes of defects found in Reheat Stretch Blow Molded PET containers. The first class of defect relates to the formation of holes in the feet and/or walls of the plastic blow molded containers during the blow molding process. The second class of defect relates to a pre-existing condition in the injection molded preform particularly in the finish area generated either in the injection process or during handling and loading of the preform on its way to the blow molding operation. These defects are identified by monitoring the sound adjacent a predetermined location along the production line of plastic blow molded containers. More specifically the defects are detected by monitoring the sound generated at the point of or within +/−30 degrees of the application of either the preblow air or the high blow air.

2. Description of the Prior Art

The leak testing of tanks, pressure vessels, and containers is an important manufacturing consideration in many different industries. In some instances, the gas-tight or liquid tight integrity of these components is usually determined by some form of a pressure-decay test. With this technique, the unit under test is injected with air to some specified overpressure, and the pressure is monitored for a specified period of time. If the pressure does not decay below a specified value at the end of the designated time period, the component under test is considered to be leak-free.

Another technique involves drawing a vacuum on the component being tested and then completely surrounding it with helium gas. A detector inside the vacuum system notifies the operator if helium is present in the air being pumped from the component.

Still another method involves the pressurization/immersion technique which consists of pressurizing the component, totally immersing the component in water or some other clear liquid, and observing the point of bubble emergence.

Yet another method utilizes a collimated beam of light which is scanned across the component under test. The test component has been pressurized with a tracer gas that strongly absorbs the light. When the light passes through the gas emerging from the source of the leak, the light energy absorbed by the gas produces an acoustic emission which is detected by a microphone. The resulting signal may be processed either as an alarm or it may be processed in coordination with the beam scanning mechanism to indicate exactly where the leak is located.

Another method involves apparatus adopted to detect the sound issued outwardly by the individual blow-molding dies during the blow-molding process wherein the sound is converted to an electrical signal and is compared with a reference signal or level and the faulty burst container is rejected.

SUMMARY OF THE INVENTION

Amongst the objectives of the present invention is to produce a method and apparatus for monitoring the production of blow molded plastic containers to detect the presence of a hole defect or a finish defect in the container during production of the containers.

Another object of the invention is to produce a method and apparatus that will detect the presence of a hole in a container being formed by a blow molding process.

Another object of the invention is to produce a method and apparatus for detecting a hole in the wall of a plastic container and producing a signal in response thereto.

The above as well as other objects of the invention may typically be achieved by a method and apparatus for monitoring the production of blow molded plastic containers comprising the steps of: introducing pressure fluid to the interior of a plastic container being formed by a blow molding process; acoustically sensing the sound of pressure fluid travelling through a defect in the plastic container being formed; producing a control signal in response to the sound produced by the pressure fluid travelling through the defect in the plastic container; and rejecting the container in response to the control signal.

The application of these techniques in themselves is relatively straightforward and easy to achieve. In the application of this technology to the real world processes, the primary difficulty arises from the problem of distinguishing the target signal from the ambient noise levels present in the typical blow molding machine.

This problem is identified in the recently issued U.S. Pat. No. 6,416,308 where it is stated that the proper setting of the signal trip level will often lead to one of two conditions. Some defective ware will be passed because the signal level generated is too low, or an excess of good ware is rejected because the trip level is set to low.

These problems are addressed in the '308 patent by turning the detector on only when a blow mold is in a sensing position and turning it back off for all other times. On a high speed rotary blow molder this method loses effectiveness because the off periods are so short—typically under one (1) second.

Other prior art disclosures attempt to resolve the issue by monitoring and storing the signals generated during normal operation and from defects and then comparing these signals through sophisticated electronics to make a determination of which ware should be rejected.

This technology solves this dilemma by four unique methods that can be utilized independently or in any combination to separate defect signals from normal operation. In addition since the occurrence of these types of defects should appear completely randomly in the blowing process, stations are tracked so that if ware from a particular station is being rejected in an inordinate amount three things will happen. First, the operator will be signaled to inspect the station in question for a possible defect such as a cracked blow nozzle, etc. Second, the operator will be permitted at the discretion of the machine owner to disable the reject output generated by the station in question. Third, a PM (preventative maintenance) notification can be generated for this station for the next maintenance day.

The unique methodologies practiced by the present invention are as follows:

First: The acoustical sensor in this operation is positioned in the area from the onset of preblow air to just after the onset of the high blow air (Typically 20 degrees to 150 degrees from the preform loading station). This allows the device to take advantage of two significant facts. In the case of the rupture of the wall of a container as it is being inflated the loudest occurrence is typically proximate the time of rupture as exemplified when over inflating a balloon to the point of rupture. In addition, if there is any contribution of air leakage such as from a worn stretch rod seal to the ambient noise level, it will be minimized since the stations prior to the position of the sensor will not be pressurized and therefore will not contribute to background noise levels.

Second: The detector may be pointed directly at the station or it may be mounted tangential to the rotation of the rotary molding wheel and with the sensing end oriented towards the oncoming blow mold. The exact orientation may vary but would typically be from exactly tangential to an angle of 45 degrees towards the center of the wheel assuming the tangential mounting location keeps the sensing device within the desired orientation to the onset of the blow air.

Third: It has been found empirically and surprisingly that the addition of a tubular extension to the sensing end of the detector acts to provide positive features. Typically an approximately one (1) inch I.D. by approximately twelve (12) inches to thirteen (13) inches long cylinder has been fitted to the end of the detector. This has been found reduce the effects of the background noise particularly when used in the orientation as described previously. In addition it can act as a resonance cavity for certain components of the target signal leading to an effective amplification of the signal under examination and an improvement in the resulting signal to noise ratio. To date only cylindrical extensions have been used, but it is believed that special geometric shapes such as a conic section might provide further improvement in the signal to noise ratio.

Fourth: Initially wide audible range sound sensors were used for a detector. Experimentation has shown that use of an ultrasonic detector outside the range of human hearing also provides significant improvement in the signal to noise ratio associated with the defective target. Typically, a center frequency of 40 kHz is selected, but the range from 20 kHz to 60 kHz appears to offer improved results.

Each of these techniques can be employed on their own merit or can be combined in various combinations for best results and minimized cost for each particular application.

The present invention concerns a method and an apparatus for monitoring the production of blow molded plastic containers formed by introducing pressure fluid to an interior of a preform in a mold cavity comprising:

a sensor means adapted to be positioned adjacent a mold cavity during the introduction of pressure fluid to a preform in the mold cavity to form a container, the sensor means being responsive to a defect sound of the pressure fluid escaping from the interior of the container for generating an output signal;

means for generating a control signal in response to the output signal whereby a container rejecter receiving the control signal rejects the container;

the sensor means including a columnator coupled to a sound detector, the columnator transmitting the defect sound from the mold cavity to the sound detector and the sound detector being responsive to the defect sound for generating the output signal;

the columnator being an elongate hollow cylinder formed of a plastic material such as polyvinyl chloride and being approximately 12.9 inches long and having an inner diameter of approximately 1.0 inch;

the columnator extending in one of a direction transverse to a path of travel of the mold cavity and a direction tangential to the path of travel of the mold cavity wherein the mold cavity travels in a generally circular path and the sensor means is positioned adjacent the path spaced in a range of from approximately 20° to approximately 150° from a preform loading station; and wherein the defect sound has a frequency in a range of approximately 20 kHz to 60 kHz and the sensor means is responsive to acoustical signals in the frequency range.

BRIEF DESCRIPTION OF THE DRAWINGS

Other objects and advantages of the invention will become readily apparent to those skilled in the art from reading the following detailed description of a preferred embodiment of the invention when considered in the light of the accompanying drawings in which.

DETAILED DESCRIPTION OF THE PREFERRED EMBODIMENT

Figure 1:
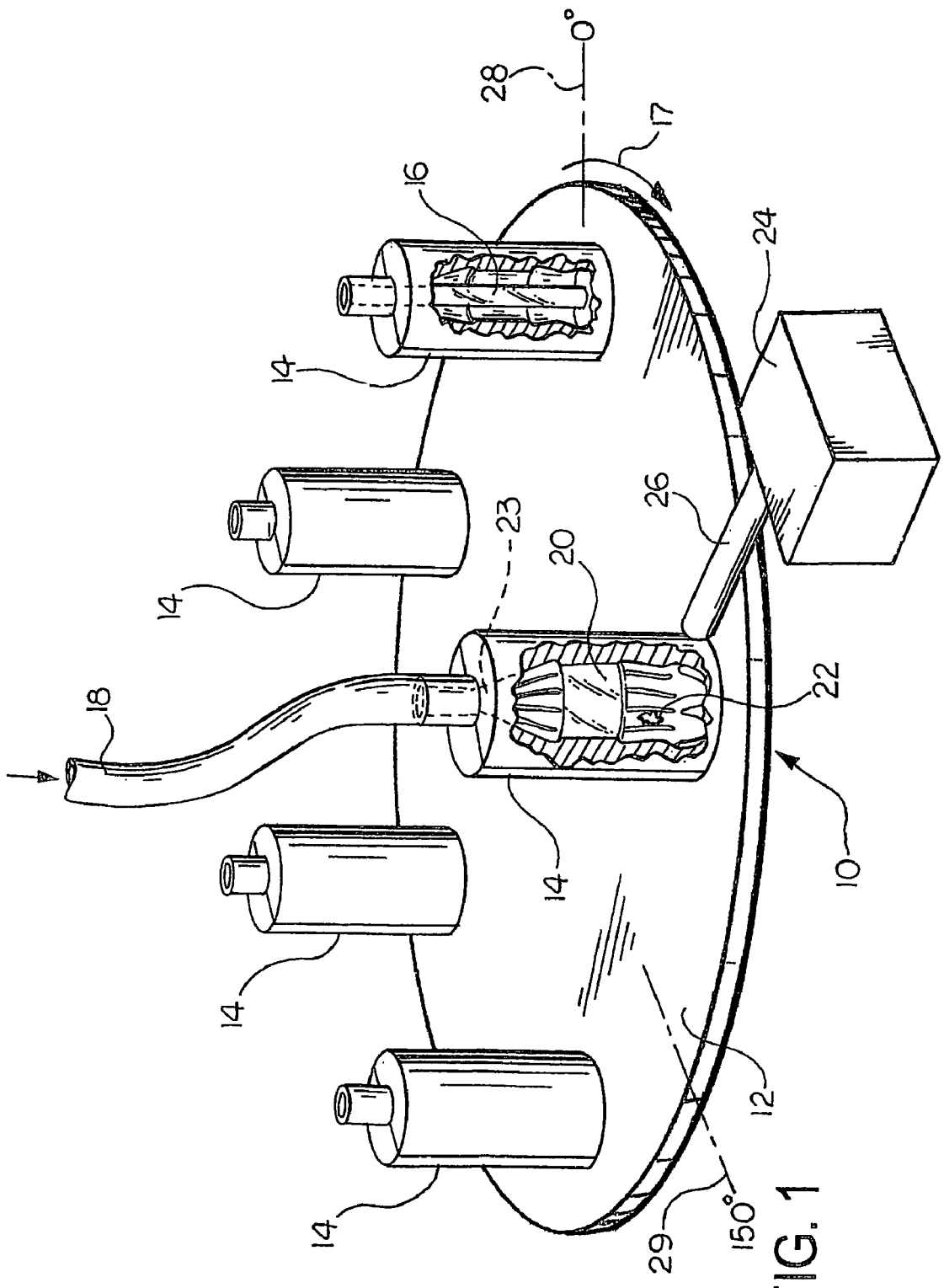
FIG. 1 is a perspective view of a columnator and a sound detector according to the present invention for sensing an acoustical signal created by the flow of pressure fluid through a hole in a container being formed during a blow molding operation.

Referring to the drawings, there is illustrated a system incorporating the features of the invention, and more particularly disclosing a station along the production line of a typical blow molding machine.

The typical blow molding machines include an annular rotatably mounted platform capable of serially receiving hollow plastic preforms or parisons. The preforms are carried in molds having an inner cavity in the desired configuration or shape of the finished container to be formed. The preforms are heated to a predetermined temperature, which prepares the plastic material to be readily blow molded. Upon reaching the desired temperature, high pressure fluid, such as compressed air, is sequentially introduced into the hollow interior of the preforms. The preforms are thereby caused to expand and assume the shape of the associated mold. The containers are caused to be inspected for defects. In the event a defective container is detected, means are provided for rejecting the container prior to filling or storage.

The completed plastic containers are then transferred, from the annular rotating platform to a conveyor which transports the containers to a filling station. Finally, the filled containers are suitably removed from the conveyor to be stored for later delivery or are immediately loaded on appropriate vehicles for delivery to the ultimate customer. Obviously, unfilled containers may also be off-loaded in a similar fashion.

There are certain instances in which, due to a myriad of reasons, the completed containers have undetected faults such as, for example, minute holes or apertures in the walls of the containers. When these faulty containers are subsequently filled with a fluid such as a carbonated beverage, disastrous results occur. Accordingly, it has become extremely important to develop a method and apparatus for the detection of these difficult to detect faults in plastic containers.

The drawings disclose an apparatus generally indicated by reference numeral 10 positioned in proximity of the annular rotating platform 12 of a blow-molding machine of the type manufactured by Sidel, a corporation of France. The rotating platform 12 contains an annular array of mold cavities 14 into which heated plastic preforms 16 are inserted. The mold cavities 14 are indexed by rotating the platform 12 in a direction indicated by an arrow 17 to a source 18 of pressure fluid, which in most instances is compressed air. The pressure fluid is introduced into the hollow interior of the heated preform 16 causing the preform to expand and assume the shape of the interior of the mold cavity 14 as a completed container 20. In the event a hole 22 is caused to be formed in the wall of the container 20, the pressure fluid from the source 18 enters an open upper end or finish 23 of the container and escapes through the hole 22 creating a predetermined acoustic signal or defect sound.

A sound detector 24 is positioned adjacent the periphery of the rotating platform 12. The input of the sound detector 24 is coupled to one end of a sound columnator 26. The sound columnator 26 is formed of a hollow plastic tube having a distal open end thereof pointed in the direction of the container 20. The sound detector 24 suitable for the purposes of the invention is commercially available and identified as a Radio Shack Sound Level Meter Model 33-2050 having an output of from 0 to 1 volt D.C.

Figure 2:
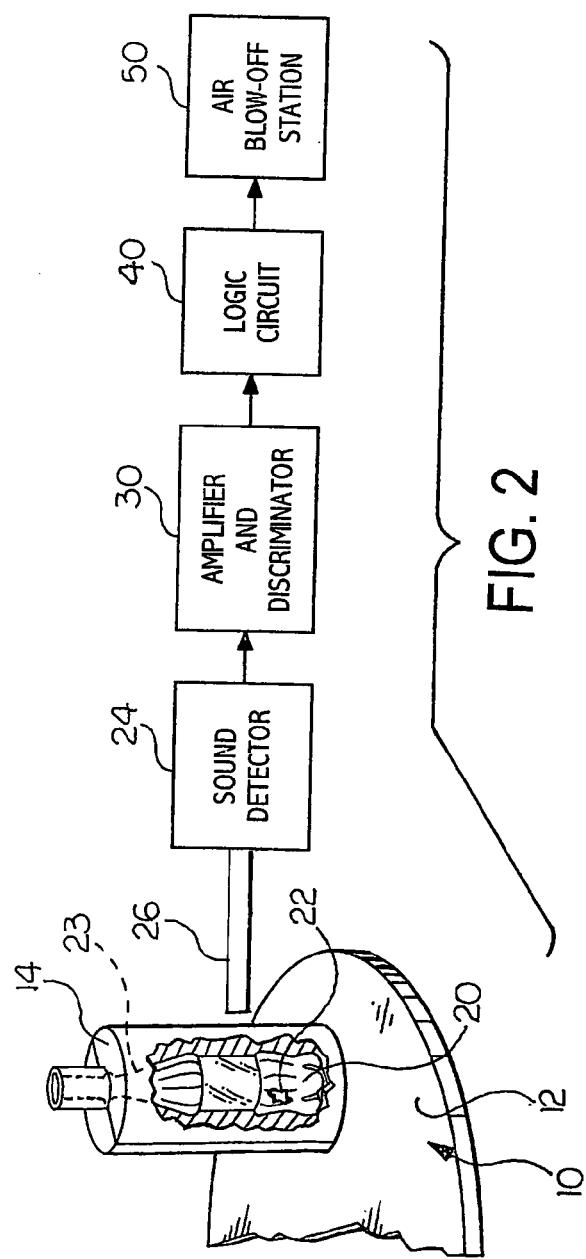
FIG. 2 is a block diagram of a system according to the present invention for sensing the hole in a plastic blow molded container during the production thereof.

As illustrated in FIG. 2, the output of the sound detector 24 is coupled to the input of an amplifier and discriminator 30 which may be set to produce an output signal based upon the amplitude of the voltage signal produced by the sound level meter which may be fed to a logic circuit 40 consisting of timing and/or counting and control logic.

The logic circuit 40 may be coupled to an air blow-off station 50 which is disposed downstream of the acoustic sensor 24 and is effective to remove any defective container 20 sensed by the logic circuit 40. Typically, the air blow-off station 50 includes solenoid operated valves controlling the flow of pressure fluid, such as compressed air for example, to forcefully eject a defective container.

It has been surprisingly discovered that the sound columnator 26 tends to both focus the transmission of defect sound energy caused by the pressure fluid flowing through the hole 22 in the container 20, but also tends to intensify the defect sound energy as it passes from the hole 22 to the sound detector 24.

Further, it has been found that satisfactory results are achieved by utilizing a plastic tube for the columnator 26. For example, a tube formed of a rigid polyvinyl chloride (PVC) material, approximately 12.9 inches in length, having a nominal I.D. of 1.0 inch, and having an O.D. of 1.3 inches, functions as a mechanical filter and signal intensifier.

In operation, the apparatus 10, as illustrated in FIG. 1, is placed adjacent the blow molding machine so that the open end of the columnator 26 coupled to the sound detector 24 faces the cavity 14 wherein the pressure fluid is injected into the heated preform 16 to cause the preform to expand to form the completed container 20.

Should the container 20 contain a fault such as the hole 22, or a void in the finish 23 of the container 20, the escaping pressure fluid flowing there through creates a characteristic acoustic signal or defect sound, sound energy in a predetermined frequency range, which enters the open end of the columnator 26 and thence travels to the sound detector 24. The sound detector 24 generates an electric signal in response to the acoustic signal and the electric signal is sent to the amplifier and discriminator circuit 30.

The signal received from the sound detector 24 is amplified and the amplified signal is sent to the logic circuit 40. The logic circuit 40 is operative to coordinate and keep track of the subsequent path of the container having the defect and will send an appropriately timed control signal to the air blow-off station 50. The station 50 contains solenoid-operated valves controlling the flow of pressurized air capable of completing the rejection operation. The pressurized air will then be appropriate to remove the container with the defect from the production line.

The unique methodologies practiced by the present invention are as follows:

First: The acoustical sensor in this operation is positioned in the area from the onset of preblow air to just after the onset of the high blow air (Typically 20° to 150° from the preform loading station). In FIG. 1 the loading station is designated by a line 28 extending radially from the center of rotation of the platform 12 which will be at zero degrees. A point 150° from the line 28 is designated by a line 29. Positioning the columnator 26 in the area between the lines 28 and 29 allows the device to take advantage of two significant facts. In the case of the rupture of the wall of a container as it is being inflated the loudest occurrence is typically proximate the time of rupture as exemplified when over inflating a balloon to the point of rupture. In addition, if there is any contribution of air leakage such as from a worn stretch rod seal to the ambient noise level, it will be minimized since the stations prior to the position of the sensor will not be pressurized and therefore will not contribute to background noise levels.

Figure 3:
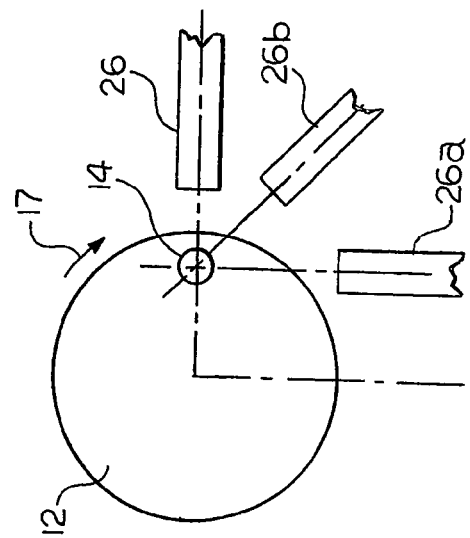
FIG. 3 is a schematic top plan view of a portion of the sensing station shown in FIG. 1 illustrating alternative mounting positions for the columnator.

Second: The columnator 26 may be pointed directly at the station or it may be mounted tangential to the rotation of the platform 12 and with the sensing end oriented towards the oncoming blow mold 14. Several mounting positions are shown in FIG. 3. The columnator 26 is shown aimed along a radial of the platform 12. The exact orientation may vary but would typically be from exactly tangential (such as a columnator 26a) to an angle of 45 degrees (such as a columnator 26b) towards the center of the wheel assuming the tangential mounting location keeps the sensing device within the desired orientation to the onset of the blow air.

Third: It has been found empirically and surprisingly that the addition of a tubular extension to the sensing end of the detector acts to provide positive features. Typically a one (1) inch ID by twelve (12) inches long cylinder 26 has been fitted to the input of the detector 24. This has been found reduce the effects of the background noise particularly when used in the orientation as described previously. In addition the columnator 26 can act as a resonance cavity for certain components of the target signal leading to an effective amplification of the signal under examination and an improvement in the resulting signal to noise ratio. To date only cylindrical extensions have been used, but it is believed that special geometric shapes such as a conic section might provide further improvement in the signal to noise ratio.

Fourth: Initially wide audible range sound sensors were used for the detector 24. Experimentation has shown that use of an ultrasonic detector outside the range of human hearing also provides significant improvement in the signal to noise ratio associated with, the defective target. Typically, a center frequency of 40 kHz is selected, but the range from 20 kHz to 60 kHz appears to offer improved results.

In accordance with the provisions of the patent statutes, the present invention has been described in what is considered to represent its preferred embodiment. However, it should be understood that the invention can be practiced otherwise than as specifically illustrated and described without departing from its spirit or scope.

What is claimed is:

1. A method for monitoring the production of blow molded plastic containers to detect a defect in any of the containers comprising the steps of:
   a. loading a preform into a mold cavity at a loading station;
   b. introducing pressure fluid to an interior of the preform in the mold cavity to form a blow molded plastic container while moving the mold cavity along a generally circular path;
   c. acoustically sensing a defect sound resulting from the pressure fluid escaping from the interior of the container being formed at a position adjacent the path and within a portion of the path from one point at onset of preblow air to another point just after onset of high blow air; and
   d. generating a control signal in response to the sensed defect sound.

2. The method defined in claim 1 wherein said step d. includes converting sound energy of the sensed defect sound to an electrical signal to generate the control signal, and further including a step of rejecting the container in response to the generation of the control signal by directing pressure fluid at the container after release from the mold cavity to remove the container from a production line.

3. The method defined in claim 1 wherein the one point is spaced approximately 20° from the loading station and the another point is spaced approximately 150° from the loading station.

4. The method defined in claim 1 wherein said step c. includes mechanically filtering sound adjacent the mold cavity to separate the defect sound from ambient sound.

5. The method defined in claim 4 wherein said mechanically filtering is performed by providing a columnator with a sensing end oriented towards the mold cavity.

6. The method defined in claim 5 wherein the columnator is formed as an elongate hollow cylinder.

7. The method defined in claim 5 wherein the columnator is formed of a plastic material.

8. The method defined in claim 7 wherein the plastic material is polyvinyl chloride.

9. The method defined in claim 5 wherein the columnator is approximately 12.9 inches long and has an inner diameter of approximately 1.0 inch.

10. The method defined in claim 5 wherein the columnator extends in a selected direction from transverse to the path to tangential to the path.

11. A method for monitoring the production of blow molded plastic containers to detect a defect in any of the containers comprising the steps of:
   a. loading a preform into a mold cavity at a loading station;
   b. introducing pressure fluid to an interior of the preform in the mold cavity to form a blow molded plastic container while moving the mold cavity along a generally circular path;
   c. acoustically sensing a defect sound resulting from the pressure fluid escaping from the interior of the container being formed at a position adjacent the path and within a portion of the path during which preblow air is being applied to the preform in the mold cavity; and
   d. generating a control signal in response to the sensed defect sound.

12. The method defined in claim 11 wherein said step c. is performed in an area from approximately 20° from the loading station and to approximately 150° from the loading station.

13. The method defined in claim 11 wherein said step c. is performed in an area from onset of the preblow air and to just after onset of high blow air.

14. The method defined in claim 11 wherein said step c. is performed by pointing a columnator in a selected direction from transverse to the path to tangential to the path.

15. The method defined in claim 11 wherein the sensing is performed in an ultrasonic frequency range having a center frequency of approximately 40 kHz.

16. The method defined in claim 11 wherein the sensing is performed in an ultrasonic frequency range of approximately 5 kHz to approximately 40 kHz.

17. An apparatus for monitoring the production of blow molded plastic containers formed by introducing pressure fluid to an interior of a preform in a mold cavity comprising:
   a columnator positioned adjacent a mold cavity during the introduction of preblow air to a preform in the mold cavity to form a container, said columnator having an input end directed toward the mold cavity;
   a sensor means being responsive a defect sound of the pressure fluid escaping from the interior of the container for generating an output signal, the defect sound being transmitted through said columnator; and
   means for generating a control signal in response to said output signal whereby a container rejecter receiving said control signal rejects the container.

18. The apparatus defined in claim 17 wherein said columnator is an elongate hollow cylinder.

19. The apparatus defined in claim 17 wherein said columnator is formed of a plastic material.

20. The apparatus defined in claim 17 wherein said columnator is approximately 12.9 inches long and has an inner diameter of approximately 1.0 inch.

* * * * *